(12) United States Patent
Osorio

(10) Patent No.: US 11,006,889 B2
(45) Date of Patent: May 18, 2021

(54) AUTOMATED MEANS TO CONTROL RESPONSES TO REPETITIVE ELECTRICAL STIMULATION AND IMPROVE THERAPEUTIC EFFICACY

(71) Applicant: Ivan Osorio, Leawood, KS (US)

(72) Inventor: Ivan Osorio, Leawood, KS (US)

(73) Assignee: Flint Hills Scientific, L.L.C., Lawrence, KS (US)

( * ) Notice: Subject to any disclaimer, the term of this patent is extended or adjusted under 35 U.S.C. 154(b) by 601 days.

(21) Appl. No.: 15/863,941

(22) Filed: Jan. 7, 2018

(65) Prior Publication Data

US 2018/0140246 A1 May 24, 2018

Related U.S. Application Data

(62) Division of application No. 14/201,482, filed on Mar. 7, 2014.

(60) Provisional application No. 61/802,140, filed on Mar. 15, 2013.

(51) Int. Cl.
*A61B 5/00* (2006.01)
*A61N 1/36* (2006.01)
*A61B 5/0484* (2006.01)

(52) U.S. Cl.
CPC .......... *A61B 5/4094* (2013.01); *A61B 5/0484* (2013.01); *A61N 1/36064* (2013.01); *A61N 1/36139* (2013.01)

(58) Field of Classification Search
CPC .. A61B 5/4094; A61B 5/0484; A61N 1/36064
See application file for complete search history.

(56) References Cited

U.S. PATENT DOCUMENTS

| | | | | |
|---|---|---|---|---|
| 8,321,030 | B2 * | 11/2012 | Maniak | A61N 1/36007 607/71 |
| 2002/0072770 | A1 * | 6/2002 | Pless | A61N 1/36064 607/2 |
| 2006/0149337 | A1 * | 7/2006 | John | A61N 1/37235 607/45 |
| 2006/0293721 | A1 * | 12/2006 | Tarver | A61N 1/36082 607/45 |

(Continued)

*Primary Examiner* — Gary Jackson
*Assistant Examiner* — Zahed Kabir
(74) *Attorney, Agent, or Firm* — CF3; Stephen Eisenmann

(57) ABSTRACT

We report a method for optimizing the therapeutic efficacy of evoked responses elicited by one or more electrical impulses delivered to a neural structure, comprising: comparing a test evoked response to an evoked response elicited by therapeutically efficacious electrical stimulation; adjusting at least one parameter of the electrical impulses in response to a determination that said test evoked response is not similar to the therapeutic evoked response; determining that the test evoked response resembles the therapeutic evoked response after performing at least one of said adjustments; and saving to memory at least one adjusted parameter that increased the similarity between the test evoked response and the therapeutic evoked response. We also report a medical device system configured to implement the method. We also report a non-transitory computer readable program storage unit encoded with instructions that, when executed by a computer, perform the method.

15 Claims, 6 Drawing Sheets

(56) References Cited

U.S. PATENT DOCUMENTS

2010/0191304 A1\* 7/2010 Scott .................... A61B 5/0476
607/45
2012/0078323 A1\* 3/2012 Osorio ............... A61N 1/36064
607/45

\* cited by examiner

AUTOMATED MEANS TO CONTROL RESPONSES TO REPETITIVE ELECTRICAL STIMULATION AND IMPROVE THERAPEUTIC EFFICACY

The present application is a divisional application of and claims the benefit to U.S. patent application Ser. No. 14/201,482, entitled "Automated Means to Control Responses to Repetitive Electrical Stimulation and Improve Therapeutic Efficacy," filed on Mar. 7, 2014 which claims the benefit under 35 U.S.C. § 119(e) of prior-filed co-pending provisional application 61/802,140, filed Mar. 15, 2013, the disclosures of patent application Ser. No. 14/201,482 and 61/802,140 are hereby incorporated by reference herein.

FIELD OF THE INVENTION

This disclosure relates to medical device systems and methods capable of detecting epileptic seizures.

SUMMARY OF THE INVENTION

Automated means to control the amplitude, latency, morphology and duration of responses evoked by repetitive electrical stimulation for control of pathological oscillations are disclosed. Methods to augment, facilitate, potentiate or generate reproducible (e.g., stereotypical) or highly variable (in a controlled fashion) responses to electrical stimuli for the purpose of preventing, blocking or reverting undesirable state transitions such as those giving way to epileptic seizures are presented.

In some embodiments, the present disclosure relates to a method for optimizing the therapeutic efficacy of evoked responses elicited by an electrical signal delivered to a neural structure, comprising: comparing a first test evoked response elicited by said electrical signal to an evoked response elicited by a prior electrical signal known to be therapeutically efficacious; adjusting at least one of an inter-pulse interval, a current magnitude, a pulse width, a pulse shape, a pulse polarity, and a pulse charge balancing of said electrical signal in response to a determination that said test evoked response is not similar to the evoked response elicited by said prior electrical signal, to provide an adjusted electrical signal; comparing a second test evoked response elicited by said adjusted electrical signal to the evoked response elicited by said prior electrical signal; and saving to memory at least one parameter of said adjusted electrical signal, if the second test evoked response has greater similarity than the first test evoked response to the evoked response elicited by said prior electrical signal.

In other embodiments, the present disclosure relates to a medical device system, comprising at least one electrical pulse generator; at least one electrode configured to deliver an electrical signal to a neural structure; at least one sensor configured to sense an evoked response of a delivered electrical signal via an evoked response unit; and a medical device, comprising: an adjustment module configured to adjust at least one parameter selected from an inter-pulse interval, a current magnitude, a pulse width, a pulse shape, a pulse polarity, or a pulse charge balancing of said electrical signal, in response to said test evoked response being insufficiently similar to the therapeutically efficacious evoked response; a therapy response analysis unit configured to determine a level of efficacy of said test evoked response; and a memory configured to store at least one said parameter of said adjusted electrical signal.

In some embodiments, the present disclosure relates to a non-transitory computer readable program storage unit encoded with instructions that, when executed by a computer, perform a method for optimizing the therapeutic efficacy of evoked responses elicited by a pulsed electrical signal delivered to a neural structure, comprising: a) applying an electrical signal defined by a plurality of electrical signal parameters to a target neural structure; b) sensing an evoked response to said electrical signal; c) comparing said evoked response to said electrical signal with an efficacious evoked response elicited by a prior electrical signal, wherein said prior electrical signal is known to be therapeutically efficacious; d) determining, based on said comparing, whether the evoked response is similar to the efficacious evoked response; e) adjusting at least one parameter of said plurality of electrical signal parameters, wherein said at least one parameter is selected from an inter-pulse interval, a current magnitude, a pulse width, a pulse shape, a pulse polarity, and a pulse charge balancing, in response to a determination that said test evoked response is not similar to the efficacious evoked response; f) repeating a)-e) until said determining results in a determination that said evoked response is similar to the efficacious evoked response; and g) saving to memory said electrical signal parameters in response to a determination that said evoked response is similar to the efficacious evoked response.

In another embodiment, the present disclosure provides a non-transitory computer readable program storage unit encoded with instructions that, when executed by a computer, perform a method for treating an epileptic seizure, comprising: receiving a time series of body data of the patient; detecting an epileptic seizure using a seizure detection algorithm, wherein said detecting is based at least on part on said body data; in response to said detecting, applying a first electrical signal tetanizing burst comprising a series of pulses to a target neural structure, wherein each of said pulses within said burst is separated from adjacent pulses by an inter-pulse interval; and applying a second electrical signal to said target neural structure, wherein said second electrical signal is selected from a single electrical pulse applied following a first waiting period ranging from 0.5 sec to 10 minutes from the preceding tetanizing pulse burst. The process may be repeated if the seizure was not blocked or attenuated. The interval (to generate the response with the highest efficacy) between the tetanizing burst and the single electrical pulse may be empirically determined.

In some embodiments, the present disclosure relates to a non-transitory computer readable program storage unit encoded with instructions that, when executed by a computer, perform a method as described above.

BRIEF DESCRIPTION OF THE DRAWINGS

The disclosure may be understood by reference to the following description taken in conjunction with the accompanying drawings, in which like reference numerals identify like elements, and in which.

Figure 1:
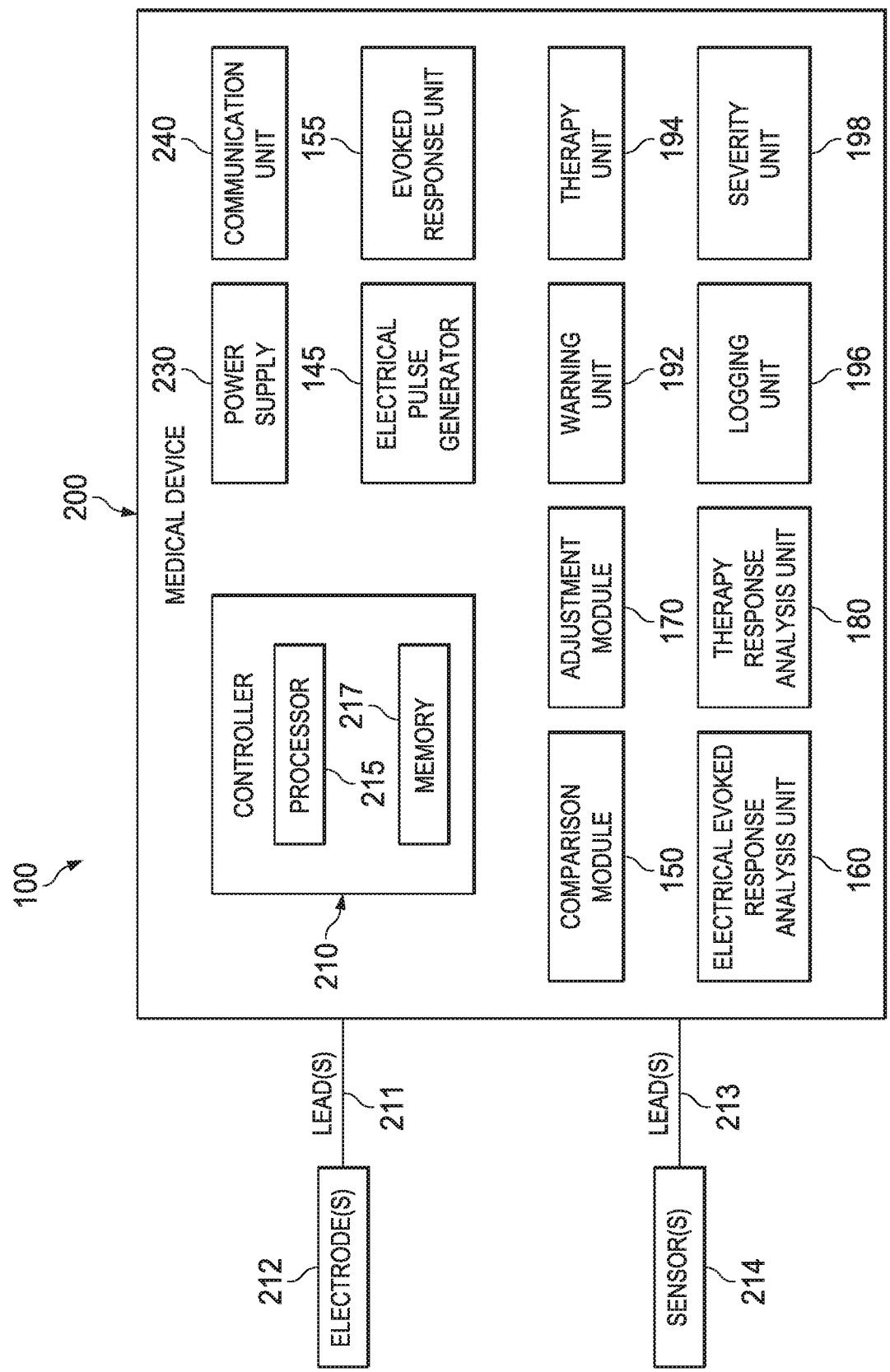
FIG. 1 shows a schematic diagram of a medical device system, in accordance with some embodiments of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are described. In the development of any actual embodiment, numerous implementation-specific decisions must be made to achieve design-specific goals, which will vary from one implementation to another. Such a development effort, while possibly complex and time-consuming, would nevertheless be a routine undertaking for persons of ordinary skill in the art having the benefit of this disclosure.

More information regarding automated assessments of therapies may be found in other patent applications assigned to Flint Hills Scientific, LLC or Cyberonics, Inc., such as, U.S. Ser. No. 12/729,093, filed Mar. 22, 2010; U.S. Ser. No. 13/280,178, filed Oct. 24, 2011; U.S. Ser. No. 13/308,913, filed Dec. 1, 2011; and U.S. Ser. No. 13/472,365, filed May 15, 2012. Each of the patent applications identified in this paragraph is hereby incorporated herein by reference.

The responses of neural tissue to repetitive electrical or magnetic stimulation differ to a certain degree from each other in amplitude, morphology, and in other features. Paired pulse facilitation and post-tetanic potentiation are among the best known examples of this phenomenon. The responses of the human brain to trans-cranial magnetic stimulation at 10 Hz. are different from each other, having a decrescendo-crescendo pattern best described by a quadratic function. In humans, evoked responses to certain repetitive stimuli differ from each other and from their averaged response, a phenomenon that according to the authors of a scientific publication indicated the evocation of a response was probabilistic and not deterministic.

Epileptogenic or pro-epileptogenic tissue may display varying responses to electrical signals, wherein the responses may include differences in inter-response characteristics (e.g., phase, amplitude and/or morphology). Repetitive therapeutic stimulation, in some cases, may cause variability in responses to those stimulations. Detailed investigation of the responses to high frequency (>100 Hz) electrical stimulation to epileptogenic tissue in rats' brain, show inter-response differences in latency (phase), amplitude and morphology. While the variability of responses evoked by repetitive stimuli does not negatively impact their value for diagnostic purposes, this may not be the case when evoked responses are used for therapeutic purposes. The effects on the phase, synchronization level, amplitude and frequency of pathological neuronal oscillations (e.g., epileptic seizures) of repetitive stimulation pulses (e.g., "trains") is likely to reflect the varying latency, amplitude and morphology (e.g., information content) of the responses it evokes. This variability which is state-dependent, may be viewed as a form of noise (probably dynamical), that is likely to alter therapeutic efficacy and the occurrence of adverse effects in a potentially uncontrollable and unpredictable fashion. This is particularly applicable to therapies whose aim is to reset the phase of, or annihilate, certain pathological oscillations such as those characterizing epileptic seizures or cardiac arrhythmias.

Some embodiments of this disclosure provide methods to minimize inter-response variability to repetitive electrical stimulation to improve efficacy of this therapeutic modality and decrease adverse effects by decreasing the variability of the latency, phase, amplitude and morphology of responses evoked by repetitive electrical stimulation.

Other embodiments of this disclosure provide magnification of the energy (e.g., amplitude) of responses to electrical currents to attenuate spatio-temporal dispersion and increase efficacy of delivery of single pulses for resetting or annihilating pathological oscillations for stimuli delivered to a site or structure remote (due to actual distance or to the existence of multiple synapses between them) from the therapeutic target.

To minimize the variability of responses evoked by repetitive stimulation, one of the intensity, waveform or inter-stimulus interval may be adjusted or changed automatically, in real-time or off-line (in-vivo, in vitro, or based on models of impulse conduction data). By either recording and analyzing the response to stimuli at the therapeutic target (e.g. epileptogenic and/or pro-epileptogenic), or its effect on the amplitude, frequency, morphology, phase and rhythmicity of the neuronal oscillations at said target, the intensity, waveform, or length of the inter-stimulus may be iteratively adjusted (manually or automatically) to decrease response variability. Conversely, inter-response variability may be enhanced when necessary to improve efficacy or reduce adverse effects.

In one embodiment of this disclosure, changes to stimulation parameters (e.g., intensity, waveform, inter-stimulus interval) may be effected using the output of a match filter as the cost function. One of the evoked responses (e.g., 1st; 5th, . . . nth) may be used as a template to which all other responses are compared.

The auto-correlation function of the template and incoming evoked responses may be computed and if its value is below a pre-specified threshold (e.g., <0.9), parameter adjustment may be automatically started. For efficiency's sake, inter-pulse interval may be the first parameter subject to change and this may be by increasing the inter-pulse interval. The choice of inter-stimulus interval as the first parameter to change and moreover the decision to lengthen (not shorten) the interval as the first step, is preferred in some embodiments, although decreasing the inter-pulse interval may be performed in other embodiments. In this non-limiting example, inter-pulse interval lengthening of a certain magnitude may be affected until the auto-correlation function value reaches the pre-specified threshold.

In another embodiment, the effect on the morphology, amplitude, phase, rhythmicity index or instantaneous frequency of pathological neuronal oscillations of an evoked response with a certain latency, amplitude, duration, morphology, number of phases and their polarity, number of minima and maxima, may be measured and changes in at least one of the parameters may be automatically performed, until the desired effect is obtained. This may be accomplished by changing one or more therapeutic electrical signal parameters to affect pathological neuronal oscillations by increasing or decreasing their amplitude (e.g., by a percentage of the observed amplitude) or frequency [within its frequency band (e.g., from 10 to 8 to Hz. or to a different frequency band (from 10 to 2 Hz)], resetting their phase (by a certain angle) or altering their rhythmicity index (e.g., decreasing it from 0.8 to 0.3). The cost function for optimization may be the desired signal feature value; in the case of the rhythmicity index, the cost function may be 0.3; inter-stimulus interval length or the amplitude of the response may be iteratively modified until said rhythmicity value is reached.

In another embodiment the effect of a single evoked response on the amplitude, frequency, morphology, phase, synchronization level or rhythmicity level of neuronal oscillations in the epileptogenic or pro-epileptogenic regions may be determined and if found to have anti-seizure effects, saved into memory for future use.

In yet another embodiment of this disclosure, the amplitude of the evoked response may be increased by adapting techniques such as paired-pulse facilitation or post-tetanic potentiation to provide improved therapies to treat pathological neuronal oscillations. In one embodiment, post-tetanic potentiation may refer to increasing the capacity of axons to release inhibitory or excitatory neurotransmitters at the synapse. These techniques may be used to enhance the therapeutic efficacy of any electro-therapy delivered to the brain, a cranial nerve, or any other nervous structures.

In one example, vagus nerve stimulation for the control of epileptic seizures is delivered at 30 Hz. for 30 sec. Based on this disclosure vagus nerve stimulation will be delivered, for example as follows: One electrical pulse followed in close temporal succession (e.g., a few up to tens of milliseconds) by another pulse of similar or different intensity, while recording both responses. Once this done, the ratio of neuronal response amplitudes is calculated (Ampl. 2nd response/Ampl. 1st response) and if the ratio is less than a value (e.g., 1.4), the current of the second pulse, the inter-pulse interval, or both are changed until the desired ratio is achieved.

In another example, the vagus nerve is stimulated electrically as follows: a short burst ("tetanus burst," e.g., 100 Hz. for 5 sec.) is followed after 0.5 sec by a single, therapeutic pulse of similar or different amplitude to the tetanus burst. The response to the single pulse is recorded and its amplitude is compared to that of a response elicited by a single unconditioned (i.e., in the absence of a preceding tetanizing burst) pulse of identical amplitude, width etc., to the single, therapeutic pulse which followed the tetanus. A ratio of amplitudes of the responses of the unconditioned pulse and of the post-tetanus (conditioned) therapeutic pulse is calculated and if it is less than a threshold value (e.g., 1.5) the tetanus amplitude, pulse width, frequency, or the time interval between it and the single pulse are automatically modified until said ratio value is achieved. A therapeutic response to a single conditioned pulse may provide feedback for modifying the tetanizing burst and/or single conditioned pulse of a subsequent performance of the technique. For example, if a response with a peak amplitude of 0.5 mA reduces the severity of a seizure by 45%, the amplitude of a subsequent conditioned pulse may be increased until the effect is 90%. In addition to the ratio of amplitudes, the area under the curve of the response or some other means of measuring its energy may be used.

While in this disclosure electrical means for modifying neural tissue responses are emphasized, chemical and thermal manipulation of neural tissue may accomplish the same or similar results.

FIG. 1 shows a schematic representation of a medical device system, according to some embodiments of the present disclosure. The medical device system 100 may comprise a medical device 200, electrode(s) 212, and lead(s) 211 coupling the electrode(s) 212 to the medical device 200. The at least one electrode 212 may be configured to deliver an electrical impulse to a neural structure, such as a cranial nerve, e.g., a vagus nerve.

The medical device system 100 may comprise at least one sensor(s) 214, each configured to collect at least one body signal from a patient relating to evoked response of the patient. Lead(s) 213 may couple the sensor(s) 214 to the medical device 200. The at least one sensor 214 may be configured to determine an evoked response of an electrical impulse delivered by electrode 212 to a neural structure.

Various components of the medical device 200, such as controller 210, processor 215, memory 217, power supply 230, communication unit 240, warning unit 192, therapy unit 194, logging unit 196, and severity unit 198 have been described in other patent applications assigned to Flint Hills Scientific, LLC or Cyberonics, Inc., such as those incorporated by reference, supra.

The memory 217 may be configured to store at least one adjusted parameter that increased the similarity between a test evoked response and a therapeutic evoked response.

The medical device 200 may comprise a comparison module 150 configured to compare a test evoked response to an evoked response also elicited by electrical stimulation and known to be therapeutically efficacious. In some embodiments, the comparison module 150 may be configured to compare at least one of latency, amplitude, morphology, duration, number and polarity of phases, number and polarity of minima, or number and polarity of maxima. In some embodiments, the comparison module 150 may implement an autocorrelation function between the test evoked response and the therapeutic evoked response. The test evoked response and the therapeutic evoked response may be considered similar if the value of an autocorrelation function is at least 0.9.

The medical device 200 may comprise an evoked response unit 155 configured to prompt the delivery of an electrical test signal for evoking a response in a tissue (e.g., vagus nerve) of a patient. The evoked response unit 155 is capable of determine various parameters for generating a test signal for prompting an evoked response. In some embodiments, the parameters for generating electrical test signals may be automatically determined based upon the desired evoked response and/or therapy efficacy data. For example, if a therapy is deemed efficacious at least up to a predetermined level, an electrical test signal may be generated based upon the parameters used for the therapeutic signal that prompted the efficacious result. In some embodiments, a look up process may be implemented to determine the parameters for the test signal. In other embodiments, external data received by the medical device 200 may be used generate the test signal. The evoked response unit 155 may provide electrical parameters to the electrical pulse generator for generating electrical test signals.

The medical device 200 may comprise a therapy response analysis unit 180 configured to analyze the response to the therapy. In one embodiment, the unit 180 may determine that level of efficacy of the therapy provided by the medical device 200. In one embodiment, this determination may be made by examining the effect of the therapy upon at least one characteristic of an epileptic event experienced by the patient. For example, the unit 180 may determine the effect of the therapy upon a seizure intensity, seizure duration, and or a seizure spread. Based upon the effect of the therapy upon at least one characteristic of the seizure event, the unit 180 may determine the level of efficacy prompted by the therapy. For example, the unit 180 may determine an efficacy index, which may provide a normalized indication of the reduction of a seizure intensity, seizure duration, and or a seizure spread resulting from the therapy. In some embodiments, a look up process may be performed, wherein the change in a characteristic of an epileptic event is compared to stored reference values to determine the efficacy index.

The medical device 200 may comprise an electrical evoked response analysis unit 160 configured to analyze the evoked response. The unit 160 may determine whether the test evoked response is sufficiently similar to the therapeutic evoked response of a therapy that was efficacious to a predetermined amount. The determination may be made using the efficacy index described above. In some embodiments, the test evoked response may be considered similar to the therapeutic response if one or more of their latency, amplitude or duration do not differ by more than 10%, and the number and polarity of phases, the number and polarity of minima, and the number and polarity of maxima are the same. Other criterions may be used to test the similarity of the test evoked response to the therapeutic response, and remain within the spirit and scope of the embodiments presented herein. If the evoked response is sufficiently similar to the response from a therapeutic signal that was sufficiently efficacious, the electrical parameters relating to the test electrical signal and the therapy signal are stored.

The medical device 200 may comprise an adjustment module 170 configured to adjust at least one parameter selected from an inter-stimulus pulse interval, a pulse intensity, a pulse width, a pulse shape, a pulse polarity, or a pulse's degree of charge balancing of said electrical impulse, in response to said test evoked response being not similar to the therapeutic evoked response.

In some embodiments, the unit 160 may determine the degree to which an evoked response resulting from a second electrical test signal resembles the response that was therapeutically efficacious. The second electrical test may be based upon a parameter adjustment made by the evoked response unit as a result of the electrical evoked response analysis unit 160.

Figure 2:
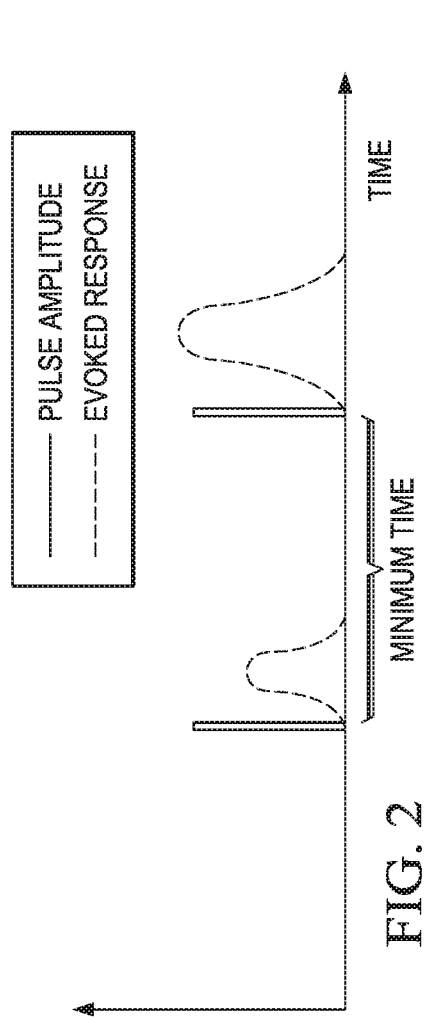
FIG. 2 shows one embodiment of an increased evoked response, in accordance with some embodiments of the present disclosure.

FIG. 2 shows a representation of paired pulse facilitation. The x-axis is time, and the y-axis shows the electrical pulse amplitude and shape applied to a neural structure (solid line) and the evoked response amplitude elicited by the electrical pulse (dotted line). A first pulse, having a first amplitude, generates a first evoked response. After a minimum time (e.g., from 1 msec to 1 minute) has elapsed, a second pulse (the conditioning pulse), having the first amplitude, generates a second, higher evoked response. As the person of ordinary skill in the art will appreciate, evoked responses and their effects are non-stationary and state dependent. For example, an electrical pulse may elicit a first evoked response when the patient is in a certain state or conditions and the same (identical) electrical pulse may elicit a second response in the same patient in a different state or under different conditions, compared to under which first response was evoked. Similarly, a certain response elicited by a first electrical pulse under certain condition, may be reproduced by a second pulse with different amplitude, shape, etc., than the first, when the second electrical pulse is delivered under different conditions than the first pulse.

By "set of conditions" is meant one or more exosomatic or endosomatic factors that may impact a patient's evoked responses to electrical or other forms (e.g. sensory) of stimulation and their therapeutic efficacy. The exosomatic factors may comprise one or more of external/environmental conditions such as time of day, time of month, luminance level, acoustic noise level, temperature signal, barometric pressure signal, etc. The endosomatic factors may comprise at least one of cortical excitability, level of consciousness (awake, asleep), physical activity of the patient and when it was performed by the patient, attention level of the patient and when the patient was attentive, cognitive activity of the patient, the type of cognitive activity and when it was performed by the patient, a signal indicative of a time elapsed since the last seizure of the patient, the last seizure type or class, the last seizure severity of the patient, a signal indicative of a time elapsed since the delivery of a therapy to the patient, the type of therapy and its dose or parameters, the efficacy of the therapy delivered to the patient, the adverse effects of the therapy and their type and severity, a signal indicative of a time elapsed since the last caloric intake and its amount, or a signal indicative of stress level and when it changes of the patient.

As used herein, two evoked responses may be considered "identical" if they look the same or similar, have the same or similar values for one or more parameters, or the like. Two evoked responses may be considered "comparable" if they have same or similar effect.

Figure 3:
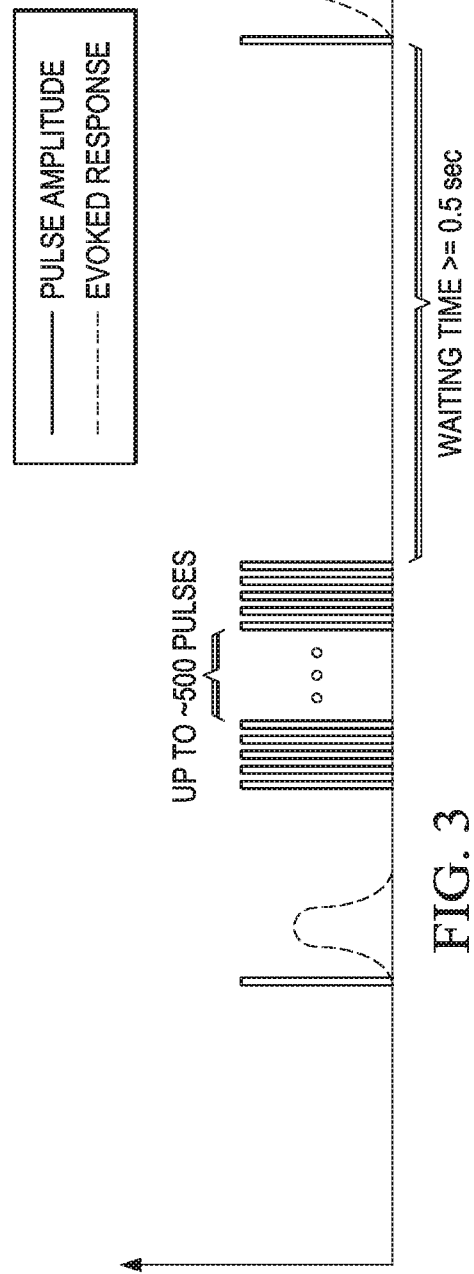
FIG. 3 shows another embodiment of an increased evoked response, according to some embodiments of the present disclosure.

FIG. 3 shows a representation of a therapeutic neurostimulation signal utilizing post-tetanic potentiation. The therapy comprises a first, multipulse phase (the tetanization phase) of electrical pulses applied to a target neural structure, a waiting time, and either a single pulse or a small number of pulses following the tetanizing phase. The therapy may be provided as an open-loop therapy, a closed-loop therapy, or as both an open-loop and a closed-loop therapy. Without being bound by theory, it is believed that the response to a post-tetanic pulse may improve therapeutic efficacy by increasing the amplitude (and reducing spatio-temporal dispersion) of neuronal responses to a single electrical pulse or a handful (e.g., 5) of pulses applied directly or indirectly to the target neural structure, thus increasing the probability of successfully annihilating pathological oscillations or resetting them into the non-pathological phase-space. Another advantage of this approach is that it may decrease the total duration of stimulation (the duty cycle).

In one embodiment, the tetanizing phase is implemented as an open-loop signal with one or more tetanizing bursts being separated by an interburst period ranging from about 0.5 seconds to several minutes (e.g., about 5 minutes), such as from about 0.5 sec to about 1 min, about 0.5 sec to about 10 sec, or about 0.5 sec to about 5 sec. A waiting period following the tetanizing phase may be implemented or determined following a seizure detection. The post-tetanic pulse(s) may be implemented as a closed-loop pulse following detection of a pathological state such as an epileptic seizure.

In another embodiment, the therapy may comprise repeated, open-loop tetanizing bursts applied to a target neural structure such as a vagus nerve or brain tissue. The tetanizing bursts may be delivered in bursts having a duration ranging from 0.5 seconds to 10 seconds, at a frequency ranging from 10 to 500 Hz, and separated from the post-tetanic pulse by a time interval ranging from 0.1 sec to 10 min. A seizure detection algorithm may be implemented to detect seizures based on one or more body data streams such as EEG data, cardiac (e.g., heart rate) data, accelerometer data, respiratory data, etc. In some embodiments, when the algorithm detects a seizure event, a tetanizing burst may be applied to the neural structure, followed by a waiting period ranging from 100 milliseconds to 5 seconds (more preferably 100 milliseconds to 1000 milliseconds, e.g., 500 milliseconds), after which a single pulse is applied to the target neural structure. In some embodiments, when the algorithm detects a seizure event, the conditioned or already tetanized nerve or brain structure may be stimulated with a single pulse. The single pulse may have a current magnitude ranging from 0.1 mA to 3.5 mA, and may comprise a pulse width from 50 microseconds to 1 millisecond.

Returning to FIG. 3, the x-axis is time, and the y-axis is both stimulus pulse amplitude (solid line) and evoked response amplitude (dotted line). A first pulse, having a first amplitude, generates a first evoked response. The first evoked response provides a point of comparison to a similar pulse applied post-tetanically. A tetanizing phase of from about 10 pulses to about 500 pulses is then delivered. After a waiting time of at least about 0.5 sec has elapsed, at least one second pulse, having the first amplitude, generates a second evoked response. As a comparison of the evoked responses makes clear, the second evoked response is higher than the first evoked response.

Though not to be bound by theory, the tetanus shown in FIG. 3 may increase the releasable pool of neurotransmitters and/or the probability of release of neurotransmitters at synaptic junctions in the neural pathway between the site of pulse delivery and the location of the evoked potential sensor.

Although FIG. 3 shows a single second pulse and second evoked response, the effects of a tetanizing burst phase may last for up to about 10 minutes. In one embodiment, the evoked response to a post-tetanic pulse may be monitored, and additional tetanizing bursts may be delivered after a later second pulse generates an evoked response less than the second evoked response shown in the figure.

Although FIGS. 2-3 are directed to evoked responses to electrical pulse delivery, other actions performed on a neural structure (e.g., drug delivery, etc.) may also lead to changes in evoked responses.

Figure 4:
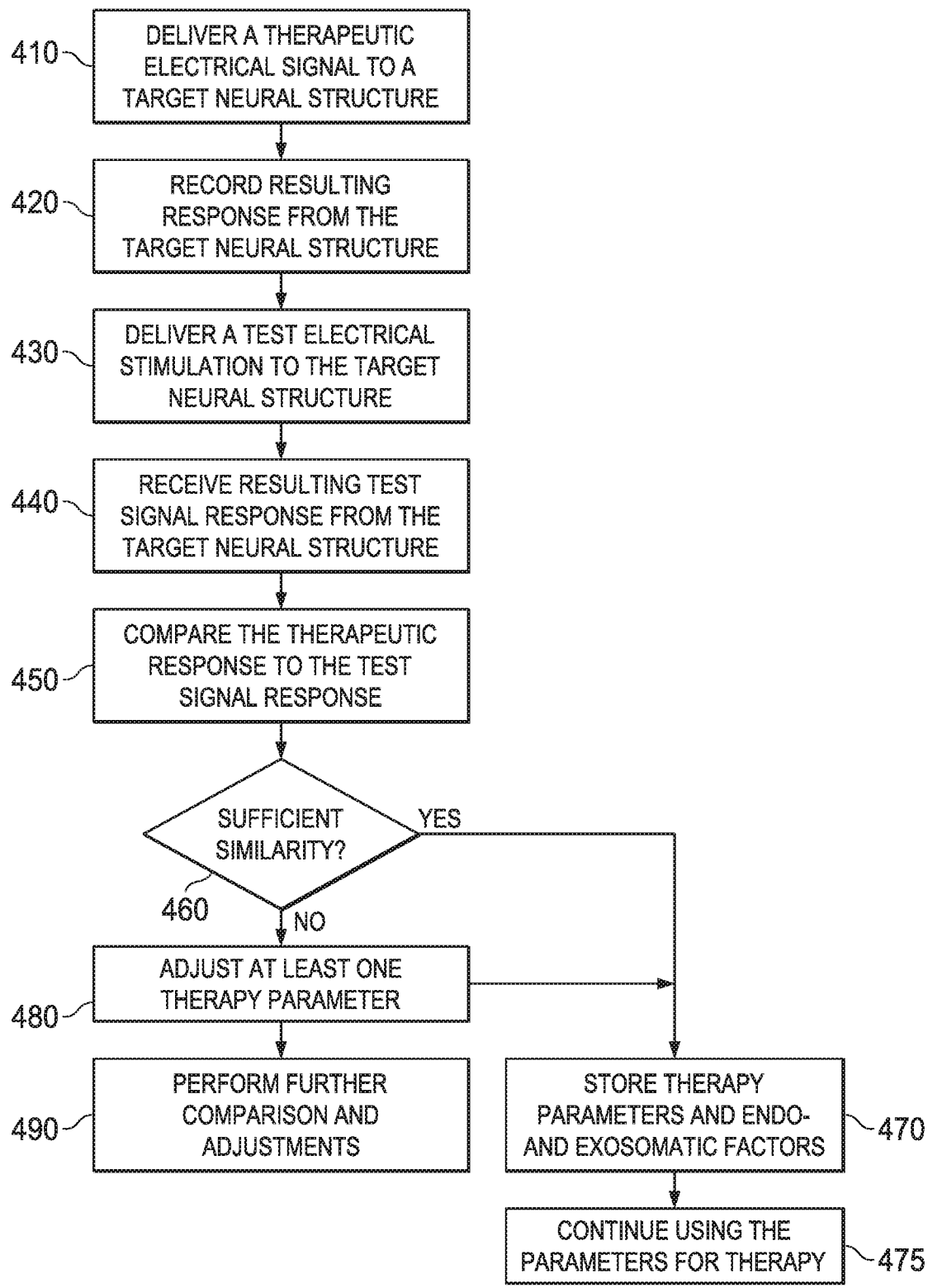
FIG. 4 shows a flowchart depiction of a method, according to some embodiments of the present disclosure.

FIG. 4 illustrates a flowchart depiction of a method 400 for adjusting a therapy based upon an evoked response, in accordance with some embodiments herein. The medical device 200 may deliver a therapeutic electrical signal to a target neural structure (e.g., a portion of the vagus nerve) of a patient (block 410). The resulting therapeutic evoked response from the target neural structure may be received and recorded (block 420). In one embodiment, the response may be received by the medical device 200 via one or more sensor 214 that are operatively coupled to the medical device 200. In other embodiments, the response may be sensed and provided to the medical device 200 by an external device. One or more characteristics of the therapeutic evoked response may be stored, such as latency, amplitude, morphology, duration, number and polarity of phases, number and polarity of minima, or number and polarity of maxima, etc. In some embodiments, the evoked response may be determined based upon body data values measured after stimulation (e.g., an evoked response by the heart to vagus nerve stimulation may be measured from heart rate instead of measuring evoked action potential on the vagus nerve). In one embodiment, the stored therapeutic evoked response may be selected from a plurality of response, wherein the selection may be based upon responses of efficacious therapy. In some embodiment, the stored responses may be categorized by the degree of efficacy.

The medical device 200 may deliver a test electrical stimulation to the target neural structure (block 430). The resulting test signal response from the target neural structure may be received (block 440).

The medical device 200 may compare one or more characteristics of one of the therapeutic responses to the test signal response (block 450). The comparison process may include comparing at least one or more of the latency, amplitude, morphology, duration, number and polarity of phases, number and polarity of minima, or number and polarity of maxima of the responses. The medical device 200 may determine whether there is sufficient similarity between the compared therapeutic and test signal responses (block 460). In one embodiment, the determination of whether there is sufficient similarity between the compared response may include determining whether one or more response characteristic described above differs by greater than 10%. Other methods (e.g., autocorrelation function, etc.) may be used to determine the sufficiency of similarity between the response characteristics. Upon a determination that there is sufficient similarity between the two compared responses, the medical device may store the therapy parameters and endo- and exosomatic factors relating to effects of the responses (block 470), and continued use of the therapy parameters for subsequent delivery of therapy (block 475). In one embodiment, storing (block 470) may further comprise storing therapy parameters and/or endo- and/or exosomatic factors relating to non-efficacious results of the therapy.

Upon a determination that there is insufficient similarity between the therapeutic response and the test signal response, an adjustment to the therapy parameter(s) may be made (block 480). The adjustment to the therapy parameter(s) may be comprise adjusting one or more of amplitude, pulse width, frequency, inter-pulse interval, etc. Upon adjustment of one or more therapy parameters, a subsequent delivery of therapy may be performed (e.g., by storing (block 470) and continuing use of the adjusted therapy parameters (block 475). In some embodiments, further comparisons of therapeutic and test signal response may be performed until a sufficient degree of correlation (e.g., an autocorrelation function of 0.9) between the responses is achieved (block 490).

Figure 5:
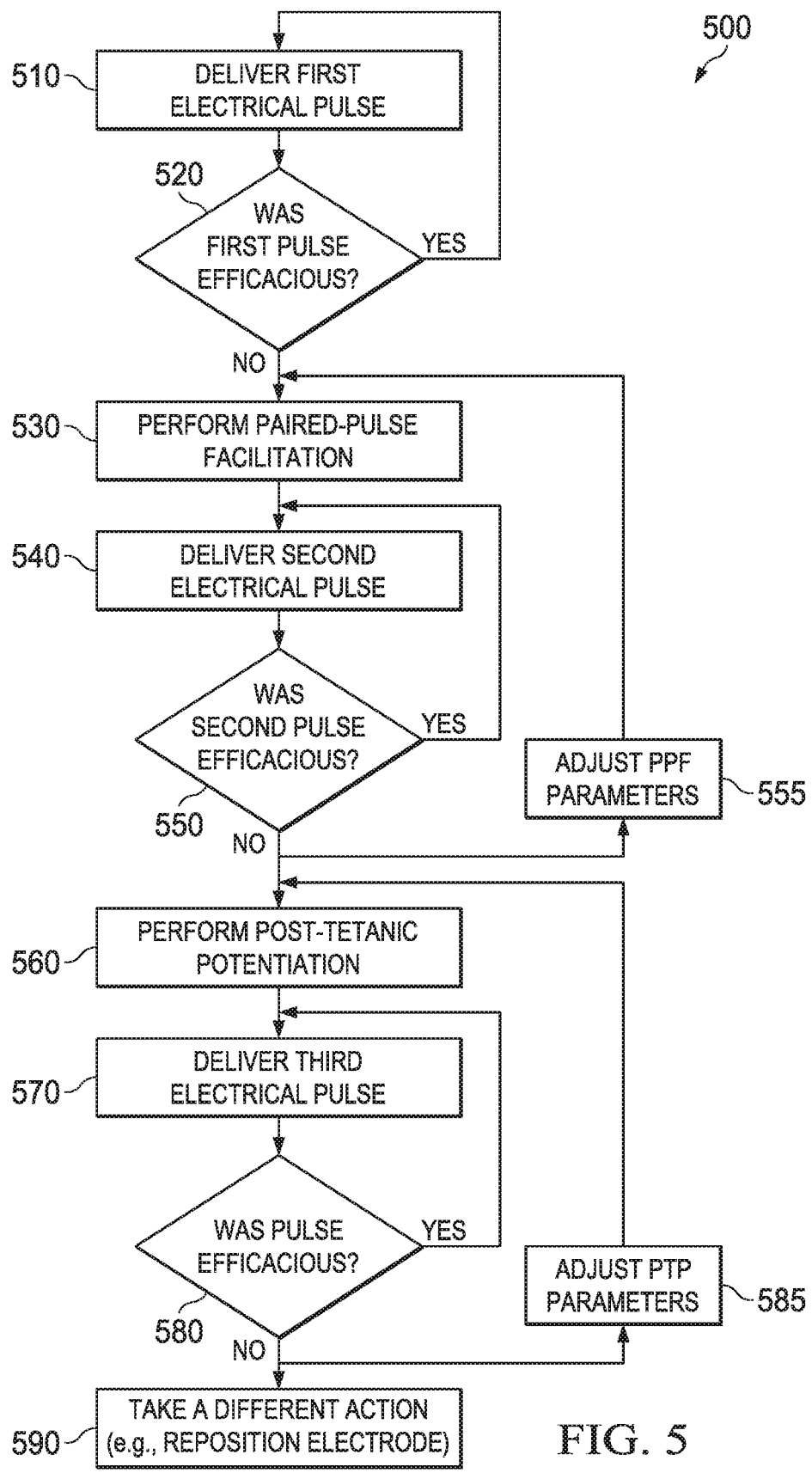
FIG. 5 shows a flowchart depiction of a method, according to some embodiments of the present disclosure.

FIG. 5 illustrates a more detailed flowchart depiction of a method for performing an adjustment of a therapy based upon an evoked response according to some embodiments of the present disclosure. A first electrical pulse is delivered (block 510) to a neural structure, such as in an ongoing therapeutic modality. If the first pulse is determined (at 520) to be efficacious, then flow may return to the delivery of the first electrical pulse (at 510).

If the first pulse is determined to lack efficacy, then paired-pulse facilitation (PPF) may be performed (block 530) and a second, post-PPF electrical pulse may be delivered (block 540). If the post-PPF pulse is determined (block 550) to be efficacious, then delivery of electrical pulses with post-PPF parameters may be continued (block 540).

If the post-PPF pulse is determined (block 550) to lack efficacy, then the method 500 may pursue either of two avenues. In one embodiment, the parameters of PPF (e.g., one or more of inter-pulse interval, current, pulse width, and pulse polarity for the PPF conditioning pulse) may be adjusted (block 555), and PPF may again be performed (block 530). In one embodiment, post-tetanic potentiation (PTP) may be performed (block 560) and a third, post-PTP electrical pulse may be delivered (at 570). If the post-PTP pulse is determined (block 580) to be efficacious, then delivery of electrical pulses with post-PTP parameters may be continued (block 570).

If the post-PTP pulse is determined (block 580) to lack efficacy, then the method 500 may pursue either of two avenues. In one embodiment, the parameters of PTP may be adjusted (block 585), and PTP may again be performed (block 560). In one embodiment, if the post-PTP pulse is determined to lack efficacy (block 580), then a different action may be taken (block 590), such as repositioning the electrode delivering the electrical pulse, reperforming PPF, redelivering a first electrical pulse, applying a different treatment type, etc.

Figure 6:
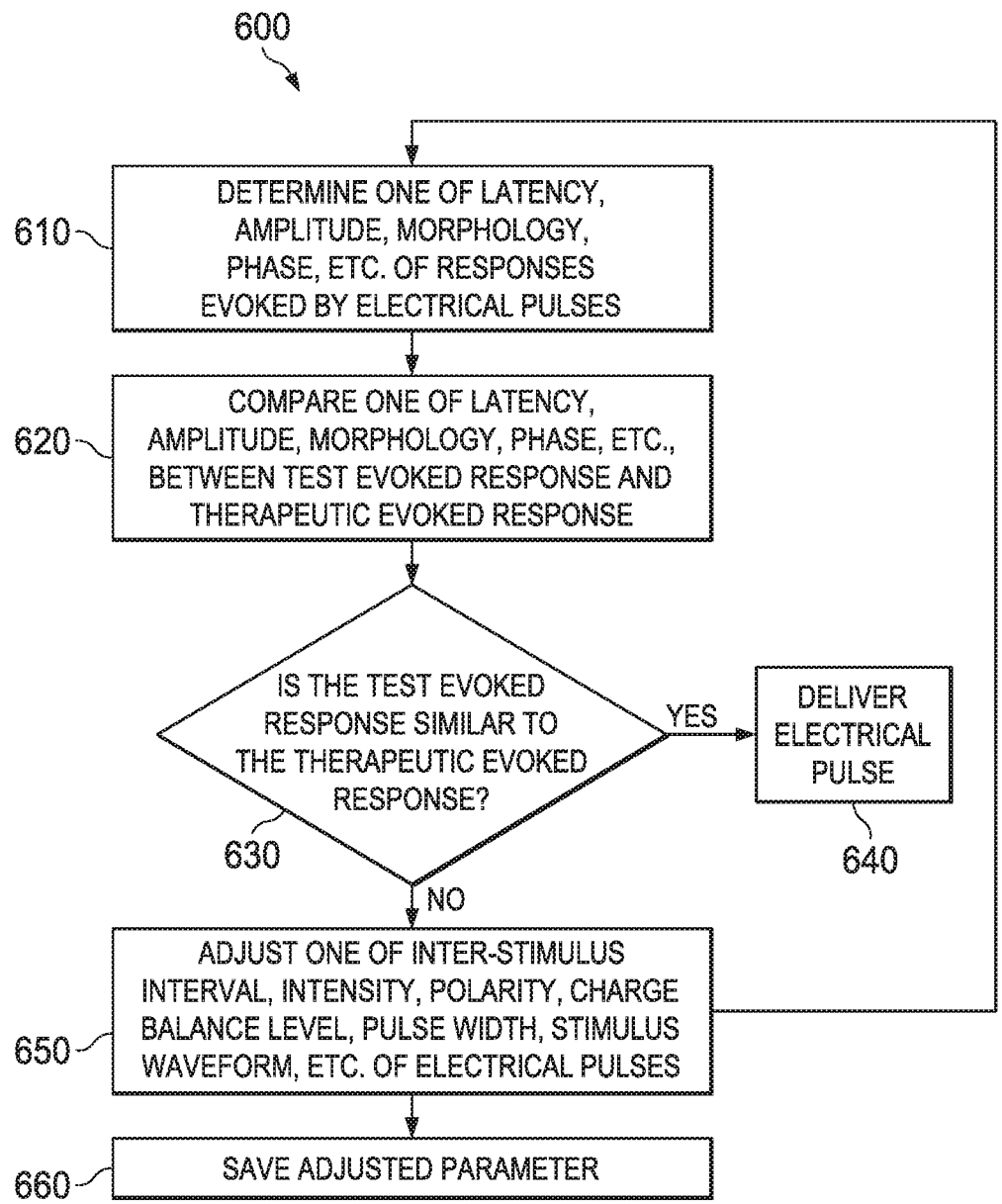
FIG. 6 shows a flowchart depiction of a method, according to some embodiments of the present disclosure.

FIG. 6 shows a flowchart representation of a method 600 according to some embodiments of the present disclosure. At least one of the latency, amplitude, morphology, phase, etc., of responses evoked by a single or repetitive electrical pulses, such as a test pulse and a known efficacious (therapeutic) pulse, may be determined (block 610). The test pulse and the known efficacious pulse may be delivered to any neural structure, such as a cranial nerve, e.g., a vagus nerve, or to any brain structure.

Once determined at block 610, the parameter(s) of the test evoked response may be compared at block 620 to an evoked response also elicited by electrical stimulation and known to be therapeutically efficacious (a "therapeutic evoked response"). In some embodiments, the comparison between the test evoked response and the therapeutic evoked response may be performed using an autocorrelation function.

If the test evoked response is determined (block 630) to be similar to the therapeutic evoked response (for example, the test evoked response may be deemed similar to the therapeutic response if one or more of their latency, amplitude or duration do not differ by more than 10%, and the number and polarity of phases, the number and polarity of minima, and the number and polarity of maxima are the same; or the test evoked response and the therapeutic response give a value of an autocorrelation function of at least 0.9), then delivery (block 640) of an electrical pulse having the parameters of the test pulse may be performed.

If the test evoked response is determined (block 630) to be dissimilar to the therapeutic evoked response, the method may comprise adjusting (block 650) at least one of an inter-stimulus pulse interval, a pulse intensity, a pulse width, a pulse shape, a pulse polarity, a pulse's degree of charge balancing in response.

Thereafter, it may be determined whether the test evoked response resembles the therapeutic evoked response after performing at least one of said adjustments to the electrical pulses delivered to a neural structure. At least one parameter that, once adjusted, increased the similarity between the test, evoked response and the therapeutic evoked response may be saved to memory (at 660) for use in generating and delivering future electrical pulses. In some embodiments, one or more parameters of the test evoked response, the therapeutic evoked response, endo- and exosomatic factors, efficacy, adverse effects, etc., may be saved to memory (block 660)

The short (<1 sec) conditioning time required to apply paired-pulse facilitation (PPF) makes it a highly useful therapy for blockage of state changes such as from non-seizure to seizure, that require for efficacy, delivery of a therapy in close temporal proximity to the onset of the change.

While post-tetanic potentiation (PTP) requires a longer conditioning period than PPF, it may be also use to block seizures and its long-life (up to 10 min. after a tetanizing pulse) may be exploited for preventing seizures or decreasing the probability of seizure recurrence which is higher shortly after the termination of a seizure. In one embodiment, conditioning tetanus (e.g., 200 Hz. for 2 sec) is delivered to a nerve or brain structure during periods associated with a high likelihood or with a high probability of occurrence of seizures. As a result, the nerve or brain structure's susceptibility to generating seizures may remain low for e.g. 5-10 min. However, if a seizure is detected, a pulse capable of evoking a large response may be delivered to the nerve or brain structure essentially immediately (e.g., within about 1-2 sec) after detection of the seizure. (Of course, it may be useful to deliver the pulse capable of evoking a large response after 1-2 sec after seizure detection).

With this approach of conditioning tetanus, seizures may be treated in close proximity to their onset, obviating the delay in delivery (of said therapy) delay imposed by the conditioning period. Means to determine the half-life of tetanization may be used to program automatically the inter-tetanus interval or measurement of the amplitude of response evokes by test pulses may be used to determine the time when the tetanus should be re-applied; this may be done in the form of dose/strength-response curves.

Figure 7:
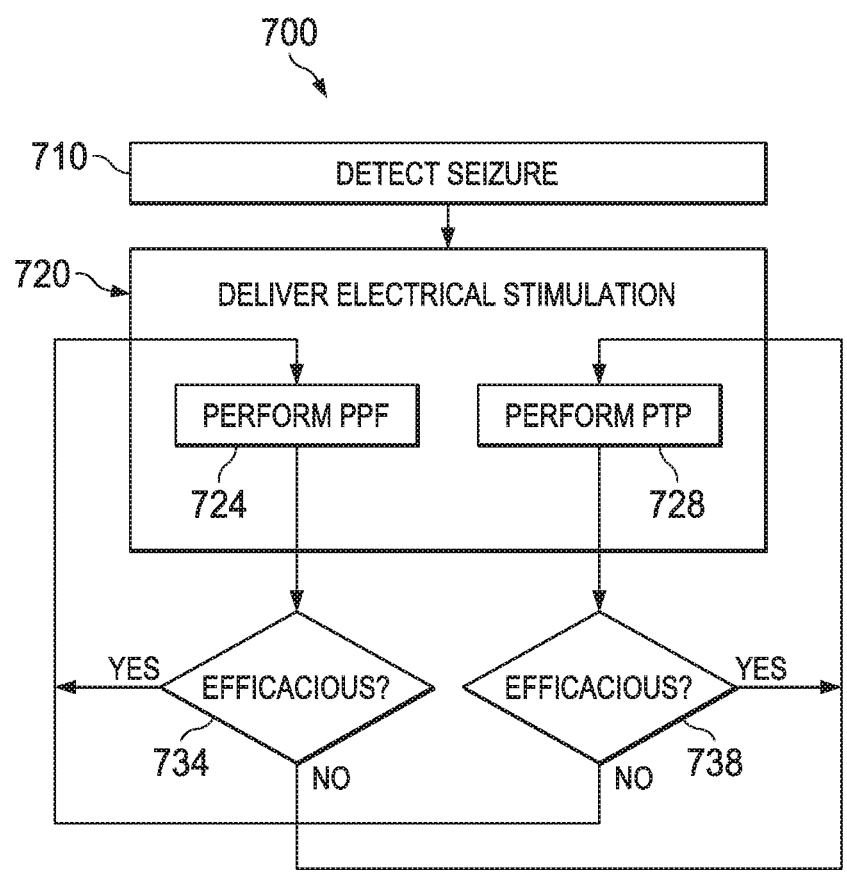
FIG. 7 shows a flowchart depiction of a method, according to some embodiments of the present disclosure.

Turning to FIG. 7, a flowchart of a method 700 is depicted. A seizure is detected (block 710). The seizure may be detected by any techniques known to the person of ordinary skill in the art, such as by the use of a cardiac-based seizure detection algorithm disclosed by one or more patents or patent applications assigned to Cyberonics, Inc., and or Flint Hills Scientific, LLC.

Upon seizure detection, electrical stimulation may be delivered (block 720). The electrical stimulation may comprise performing PPF (block 724), performing PTP (block 728), and/or other forms of electrical stimulation (not shown). PPF and PTP may be performed as described elsewhere herein.

If PPF is performed (block 724), then its efficacy may be determined (block 734). If PPF is found to be efficacious, PPF may be continued (block 724). If PPF is found to lack efficacy, than PTP may be performed (block 728). Similarly, if PTP is performed (block 728), then its efficacy may be determined (block 738). If PTP is found to be efficacious, PTP may be continued (block 728). If PTP is found to lack efficacy, than PPF may be performed (block 724). As should be apparent, if PPF or PTP leads to blockage or abatement of the seizure, then it may be discontinued and the method 700 may return to seizure detection at block 710.

The methods depicted in FIGS. 4-7 and/or described above may be governed by instructions that are stored in a non-transitory computer readable storage medium and that are executed by, e.g., a processor 217 of the medical device 200. Each of the operations shown in FIGS. 4-7 and/or described above may correspond to instructions stored in a non-transitory computer memory or computer readable storage medium. In various embodiments, the non-transitory computer readable storage medium includes a magnetic or optical disk storage device, solid state storage devices such as flash memory, or other non-volatile memory device or devices. The computer readable instructions stored on the non-transitory computer readable storage medium may be in source code, assembly language code, object code, or other instruction format that is interpreted and/or executable by one or more processors.

In some embodiments, the present disclosure may relate to one or more of the following numbered paragraphs:

A non-transitory computer readable program storage unit encoded with instructions that, when executed by a computer, perform a method for treating an epileptic seizure, comprising: receiving a time series of body data of a patient; detecting an epileptic seizure using a seizure detection algorithm, wherein said detecting is based at least on part on said body data; and in response to said detecting, administering to said patient a drug configured to potentiate a target neural structure, and applying an electrical signal to said target neural structure subsequent to said administering, wherein the electrical signal elicits an evoked response.

What is claimed:

1. A method utilizing a medical device, the medical device including one or more processors configured to implement the method for treating an epileptic seizure, the method comprising:
   receiving a time series of body data of a patient;
   detecting the epileptic seizure using a seizure detection algorithm, wherein the detecting is based at least on part on the time series of body data;
   applying a first electrical pulse to a target neural structure of the patient, wherein the first electrical pulse elicits a first evoked response;
   applying a second electrical pulse to the target neural structure, following a first waiting period ranging from 1 millisecond to 1 minute after applying the first electrical pulse, wherein the second electrical pulse elicits a second evoked response having a higher amplitude than the first evoked response.

2. The method of claim 1, wherein the method further comprising:
   determining, following the second electrical pulse, whether or not the epileptic seizure has been terminated; and
   in response to a determination that the epileptic seizure has not been terminated, applying a third electrical pulse to the target neural structure following a second waiting period ranging from 1 millisecond to 1 minute after applying the second electrical pulse.

3. The method of claim 1, wherein the method further comprising:
   determining, following the second electrical pulse, whether or not the epileptic seizure has been terminated; and
   in response to a determination that the epileptic seizure has not been terminated, administering an alternative therapy to the patient.

4. The method of claim 1, wherein the target neural structure is a vagus nerve, a trigeminal nerve, a hypoglossal nerve, a glossopharyngeal nerve, or a brain structure.

5. A method utilizing a medical device, the medical device including one or more processors configured to implement the method for treating an epileptic seizure, the method comprising:
   receiving a time series of body data of a patient;
   detecting the epileptic seizure using a seizure detection algorithm, wherein the detection is based at least on part on the time series of body data; and
   in response to the detection, initiating a treatment including:
   applying a first, open-loop electrical signal comprising one or more series of tetanizing pulse bursts to a target neural structure, wherein each of the tetanizing pulse burst is separated from adjacent tetanizing pulse burst by an interburst period; and
   applying a second electrical signal to the target neural structure, wherein the second electrical signal is a single electrical pulse applied following a first waiting period ranging from 0.1 seconds to 10 minutes from an immediately preceding tetanizing pulse burst; and
   repeating the treatment if the epileptic seizure is not terminated by the treatment;
   wherein delivery of the second electrical signal is selected based on a time elapsed since the immediately preceding tetanizing pulse burst at a time of the seizure detection.

6. The method of claim 5, wherein each of the tetanizing pulse bursts comprises a burst duration of from 0.1 seconds to 1 second, a pulse frequency of from 100 Hz to 1500 Hz, and a current amplitude of from 0.01 mA to 10.0 mA.

7. The method of claim 5, further comprising determining, following the single electrical pulse, whether or not the epileptic seizure has been terminated; and
   in response to a determination that the epileptic seizure has not been terminated, applying a second single electrical pulse to the target neural structure.

8. The method of claim 5, wherein the target neural structure is a cranial nerve or a brain structure.

9. The method of claim 5, wherein the interburst period is from about 0.1 seconds to about 2 seconds.

10. The method of claim 5, wherein the interburst period is from about 2.1 seconds to 10 seconds.

11. The method of claim 5, wherein a burst duration is from about 0.1 seconds to 2 seconds.

12. A method utilizing a medical device, the medical device including one or more processors configured to implement the method for treating an epileptic seizure, the method comprising:
   receiving via the one or more processors one or more body data streams;
   detecting the epileptic seizure based on the one or more body data streams;
   applying a first tetanizing phase to a neural structure; and
   applying a second electrical pulse to the neural structure where the second electrical pulse is applied to the neural structure after a first waiting period from a delivery of a first electrical burst to the neural structure;
   wherein at least one of the first tetanizing phase and the second electrical pulse are utilized to treat the epileptic seizure;
   wherein a first response from the first electrical burst is lower in amplitude or duration than a second response from the second electrical burst.

13. The method of claim 12, wherein the first tetanizing phase includes 10 to 1,500 pulses.

14. The method of claim 12, wherein the first waiting period is from about 0.1 seconds to about 2 seconds.

15. The method of claim 12, wherein the first waiting period is from about 2.1 seconds to about 10 seconds.

* * * * *